(12) United States Patent
Thill et al.

(10) Patent No.: US 12,005,170 B2
(45) Date of Patent: Jun. 11, 2024

(54) PRIMING OF SPINNING MEMBRANE SEPARATORS

(71) Applicant: Fenwal, Inc., Lake Zurich, IL (US)

(72) Inventors: Melissa A. Thill, Kenosha, WI (US); Amit J. Patel, Algonquin (IL)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 17/541,604

(22) Filed: Dec. 3, 2021

(65) Prior Publication Data

US 2022/0176025 A1 Jun. 9, 2022

Related U.S. Application Data

(60) Provisional application No. 63/122,106, filed on Dec. 7, 2020.

(51) Int. Cl.
*A61M 1/26* (2006.01)
*B01D 63/16* (2006.01)

(52) U.S. Cl.
CPC .............. *A61M 1/265* (2014.02); *B01D 63/16* (2013.01)

(58) Field of Classification Search
CPC ............ A61M 1/265; A61M 2205/103; A61M 1/3603; A61M 1/3643; A61M 1/3693; A61M 1/029; B01D 63/16; B01D 2315/02; B01D 2323/42; B01D 2323/50; B01D 67/0088
See application file for complete search history.

(56) References Cited

U.S. PATENT DOCUMENTS

| | | |
|---|---|---|
| 4,919,817 A | 4/1990 | Schoendorfer et al. |
| 5,298,016 A | 3/1994 | Gordon |
| 5,460,715 A | 10/1995 | Kawamura et al. |
| 5,868,696 A | 2/1999 | Giesler et al. |
| 5,989,441 A | 11/1999 | Rashidbaigi et al. |
| 6,251,284 B1 | 6/2001 | Bischof et al. |
| 6,348,156 B1 | 2/2002 | Vishnoi et al. |
| 6,419,822 B2 | 7/2002 | Muller et al. |
| 6,527,957 B1 | 3/2003 | Deniega et al. |

(Continued)

FOREIGN PATENT DOCUMENTS

| | | |
|---|---|---|
| EP | 0310205 A2 | 4/1989 |
| EP | 1484390 A1 | 12/2004 |
| WO | WO 2018/053217 A1 | 3/2018 |

OTHER PUBLICATIONS

Extended European Search Report, dated Apr. 20, 2022, for application No. EP21212151.1-1113.

*Primary Examiner* — Krishnan S Menon
(74) *Attorney, Agent, or Firm* — Cook Alex Ltd.

(57) ABSTRACT

During a first stage of a priming procedure, a priming fluid is conveyed into a spinning membrane separator via a filtrate outlet port so as to convey air out of the spinning membrane separator via an inlet port and a retentate outlet port of the spinning membrane separator. During an optional second stage of the priming procedure, the priming fluid is conveyed into the spinning membrane separator via the inlet port so as to convey air out of the spinning membrane separator via the retentate outlet port. A rotor positioned within a housing of the spinning membrane separator may be rotated with respect to the housing during the first and second stages to force air from within the rotor into an annulus defined between the rotor and the housing for more complete priming of the spinning membrane separator.

22 Claims, 7 Drawing Sheets

(56) References Cited

U.S. PATENT DOCUMENTS

| | | |
|---|---|---|
| 8,556,793 B2 | 10/2013 | Foley et al. |
| 9,284,529 B2 | 3/2016 | Kusters et al. |
| 9,388,383 B2 | 7/2016 | Kusters et al. |
| 2008/0251433 A1 | 10/2008 | Kim et al. |
| 2011/0180495 A1 | 7/2011 | Schoendorfer |
| 2012/0220915 A1 | 8/2012 | Wegener et al. |
| 2016/0144098 A1 | 5/2016 | Radwanski et al. |
| 2018/0361054 A1 | 12/2018 | Roxas |
| 2019/0369008 A1 | 12/2019 | Kusters |

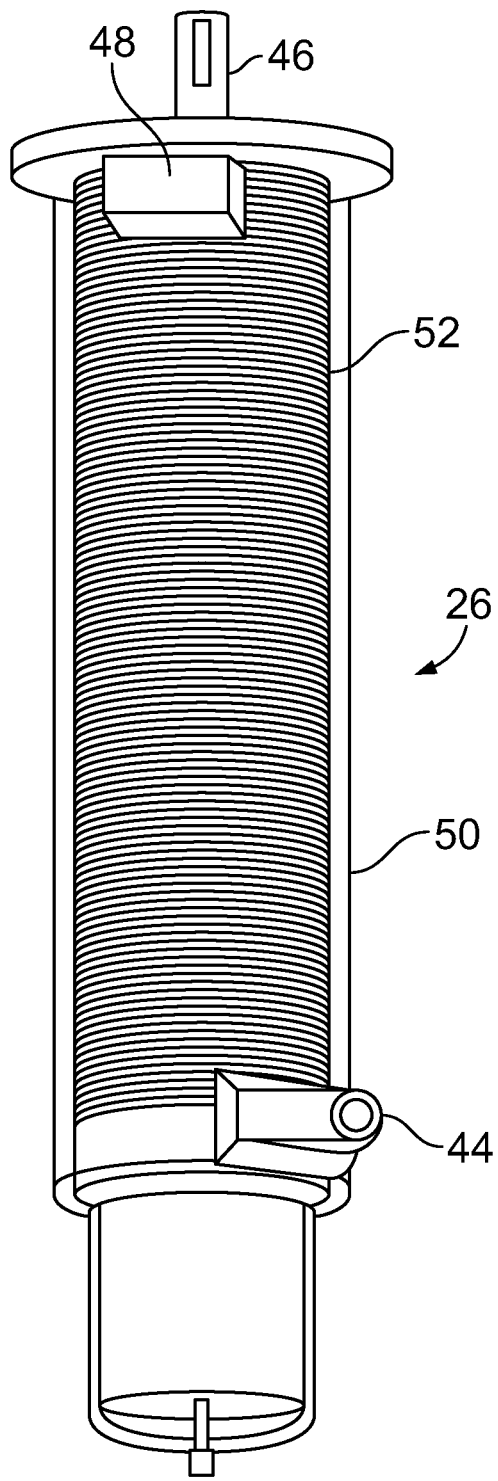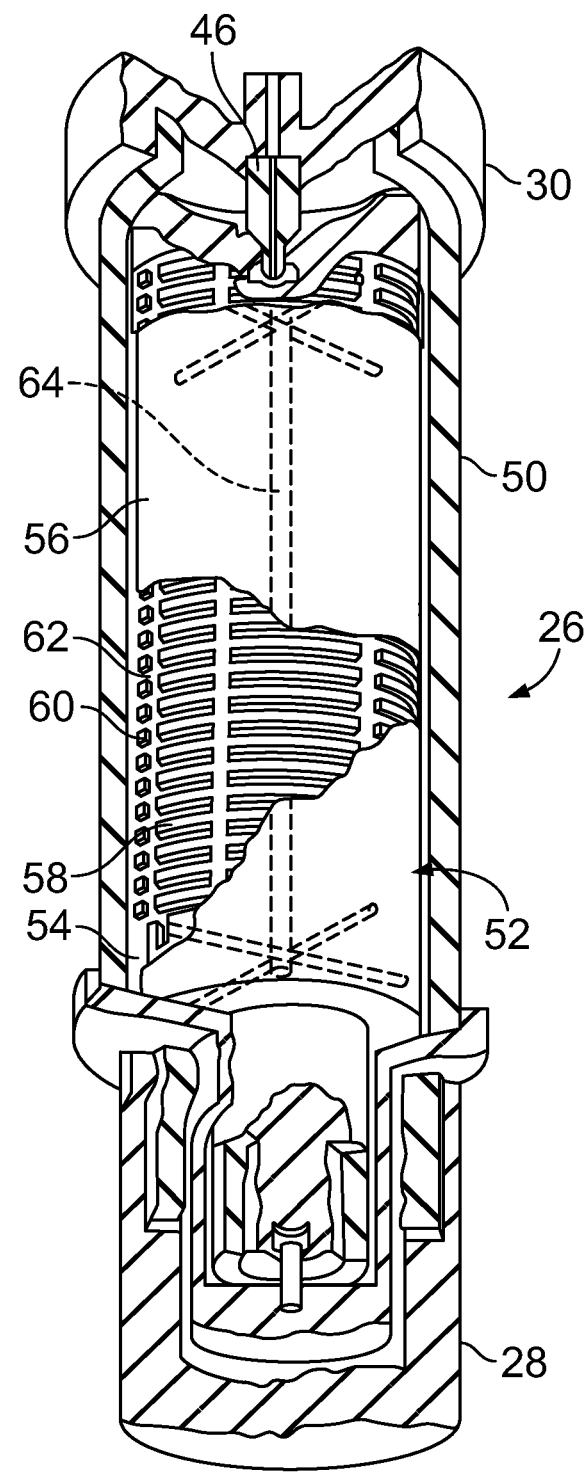
FIG. 6      FIG. 7

PRIMING OF SPINNING MEMBRANE SEPARATORS

CROSS-REFERENCE TO RELATED APPLICATIONS

This application claims the benefit of and priority of U.S. Provisional Patent Application Ser. No. 63/122,106, filed Dec. 7, 2020, the contents of which are incorporated by reference herein.

BACKGROUND

Field of the Disclosure

The invention relates to spinning membrane separation devices. More particularly, the invention relates to systems and methods for priming spinning membrane separation devices.

Description of Related Art

Various blood processing systems now make it possible to collect particular blood constituents, rather than whole blood, from a blood source. Typically, in such systems, whole blood is drawn from a source, the particular blood component or constituent is removed and collected, and the remaining blood constituents are returned to the source.

Whole blood is frequently separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow circuit during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid flow circuit that is mounted in cooperation on the hardware. The centrifuge assembly engages and spins a disposable centrifuge chamber of the fluid flow circuit during a collection procedure. The blood, however, makes actual contact only with the fluid flow circuit, which assembly is used only once and then discarded.

While many of the prior blood separation apparatus and procedures have employed centrifugal separation principles, there is another class of devices, based on the use of a membrane, that has been used for (among other things) cell washing and separating plasma from cellular blood components. A system incorporating both a centrifuge and a spinning membrane separator is described in POT Patent Application Publication No. WO 2018/053217 A1, which is hereby incorporated by reference herein.

Spinning membrane separators employ relatively rotating surfaces, at least one of which carries a porous membrane. Typically, a spinning membrane separator includes an outer stationary housing and an internal spinning rotor covered by a porous membrane. Fluid (e.g., blood or platelet-rich plasma) is fed into an annular gap or annulus defined between the rotor and the housing. The fluid moves along the longitudinal axis of the housing toward an exit region, with the filtrate (e.g., plasma) passing through the membrane and out of the housing via an outlet port aligned with the rotational axis of the rotor. The remaining fluid components or retentate (which will be cellular blood components, in the case of blood or platelet-rich plasma being processed by the spinning membrane separator) move to the exit region between the rotor and the housing and then exit the housing via an outlet port fluidly connected to the annulus.

Spinning membrane separators have been found to provide excellent plasma filtration rates or separation efficiencies, due primarily to the unique flow patterns ("Taylor vortices") induced in the annulus between the spinning rotor and the housing. The Taylor vortices help to keep the blood cells from depositing on and fouling or clogging the membrane.

As with any other component of a disposable fluid flow circuit, it is advantageous to prime a spinning membrane separator prior to use in order to remove air and, in the case of the spinning membrane separator, wet the membrane. This is important because an air bubble trapped between the membrane and the ribs of the rotor creates a region of the membrane that is unusable during separation. According to one conventional approach to priming a spinning membrane separator, which is described in U.S. Pat. No. 9,388,383 (which is hereby incorporated by reference herein), a spinning membrane separator is oriented vertically, with its filtrate outlet port facing upwardly. A priming fluid is introduced into the housing via the inlet port (which is positioned adjacent to the bottom end of the spinning membrane separator in this orientation), with the fluid-air interface advancing upwardly and air being expelled through either or both of the retentate outlet port and the filtrate outlet port.

In one version of the approach described in U.S. Pat. No. 9,388,383 (which version is illustrated in FIGS. 1A-1C), the filtrate outlet port L is initially closed, with priming fluid entering the housing U via the inlet port N and exiting the housing U via the retentate outlet port R (FIG. 1A), which fills the annulus G with priming fluid. Next, the retentate outlet port R is closed and the filtrate outlet port L is opened (FIG. 1B), which directs the priming fluid (still being conveyed into the housing U via the inlet port N) out of the housing U via the filtrate outlet port L, thereby priming through the membrane E. Finally, the filtrate outlet port L is closed again, while the retentate outlet port R is opened (as in the initial stage), with priming fluid moving through the spinning membrane separator D from the inlet port N to the retentate outlet port R (FIG. 1C), which re-primes the annulus G and removes additional air pockets and bubbles.

In a variation of the preceding multi-stage approach (which variation is shown in FIGS. 2A-2D), the first two stages proceed as described above, with priming fluid entering the housing U via the inlet port N and exiting via only the retentate outlet port R (FIG. 2A) and then via only the filtrate outlet port L (FIG. 2B). In a third stage (which is shown in FIG. 2C), the flow of priming fluid into the housing U via the inlet port N is stopped, while the flow of priming fluid out of the housing U via only the filtrate outlet port L continues (by operation of a pump associated with the filtrate outlet port L), which creates a vacuum. This builds negative pressure within the spinning membrane separator D to reduce air bubbles. This pressure is relieved by opening the inlet port N. Once the pressure has been relieved, the inlet port N is closed again, with the filtrate outlet port L also being closed, while the retentate outlet port R is open, as shown in FIG. 20. The priming fluid is pulled out of the housing U via the retentate outlet port R (by operation of a pump associated with the retentate outlet port R), which again creates a vacuum and builds negative pressure within the spinning membrane separator D to reduce air bubbles. Finally, the inlet port N is opened to relieve the pressure within the now-primed spinning membrane separator D.

According to yet another conventional approach, the spinning membrane separator is not fully primed before separation begins. In such an approach, priming fluid is pumped toward the inlet port of the spinning membrane separator, but not into the inlet port. A fluid to be separated is then pumped toward the inlet port, which forces the priming fluid into the spinning membrane separator via the inlet port, ahead of the fluid to be separated. The priming fluid flows upwardly through the spinning membrane separator and out of the filtrate and retentate outlet ports, just ahead of the fluid to be separated, such that the spinning membrane separator is being primed while separation takes place. This approach is intended to reduce the amount of priming fluid used to prime the membrane.

While these approaches to priming a spinning membrane separator have proven effective (resulting in approximately 90% of the membrane being primed, in some cases), it would be advantageous to provide alternative approaches that are capable of consistently priming an even greater portion of the membrane.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing device includes a controller and a pump system. The fluid processing device also includes a spinning membrane separator drive unit that is configured to receive a spinning membrane separator having a housing, a rotor rotatably received within the housing, an inlet port, a filtrate outlet port in fluid communication with an interior of the rotor, and a retentate outlet port in fluid communication with an annulus defined between the housing and the rotor. The controller is configured to execute a priming procedure, which includes controlling the pump system during a first stage to convey a priming fluid into the spinning membrane separator via the filtrate outlet port so as to convey air out of the spinning membrane separator via the inlet port and the retentate outlet port. The controller ends the first stage and then may control the pump system during an optional second stage to convey the priming fluid into the spinning membrane separator via the inlet port so as to convey air out of the spinning membrane separator via the retentate outlet port.

In another aspect, a method is provided for priming a spinning membrane separator including a housing, a rotor rotatably received within the housing, an inlet port, a filtrate outlet port in fluid communication with an interior of the rotor, and a retentate outlet port in fluid communication with an annulus defined between the housing and the rotor. The method includes conveying a priming fluid into the spinning membrane separator via the filtrate outlet port during a first stage so as to convey air out of the spinning membrane separator via the inlet port and the retentate outlet port. The first stage is ended and then may be followed by an optional second stage in which the priming fluid is conveyed into the spinning membrane via the inlet port so as to convey air out of the spinning membrane separator via the retentate outlet port.

BRIEF DESCRIPTION OF THE DRAWINGS

FIG. 6 is a perspective view of an exemplary spinning membrane separator of a fluid flow circuit;

FIG. 7 is a perspective view of the spinning membrane separator of FIG. 6 and a portion of a spinning membrane separator drive unit, with portions of both being cut away for illustrative purposes;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 3-9 show components of a blood or fluid processing system that embodies various aspects of the present subject matter. While the system may be described herein in terms of its use in processing blood or a blood component, it should be understood that systems according to the present disclosure can be used for processing a variety of biological or bodily fluids (including fluids containing both bodily and non-bodily fluids, such as anticoagulated blood), as well as non-bodily fluids.

Figure 1A:
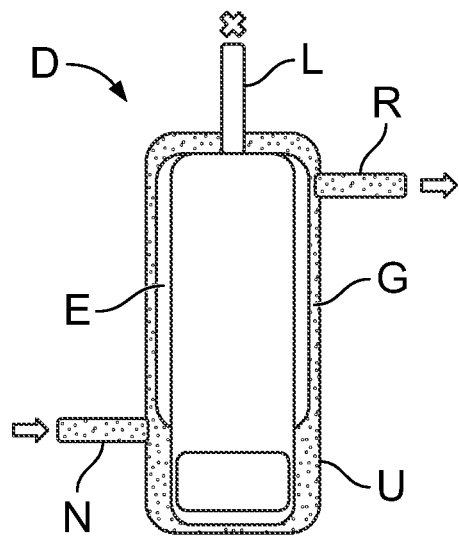
FIGS. 1A-1C illustrate a first conventional approach to priming a spinning membrane separator.
Figure 1B:
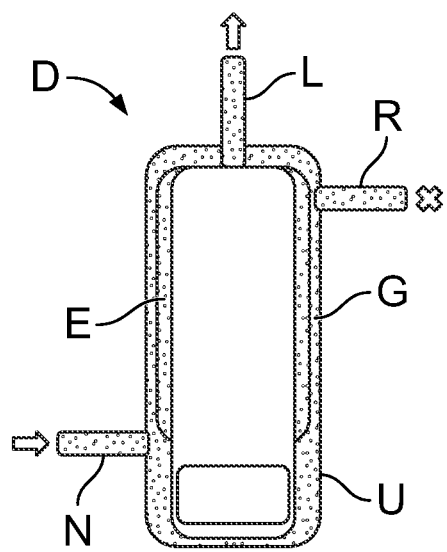
Figure 1C:
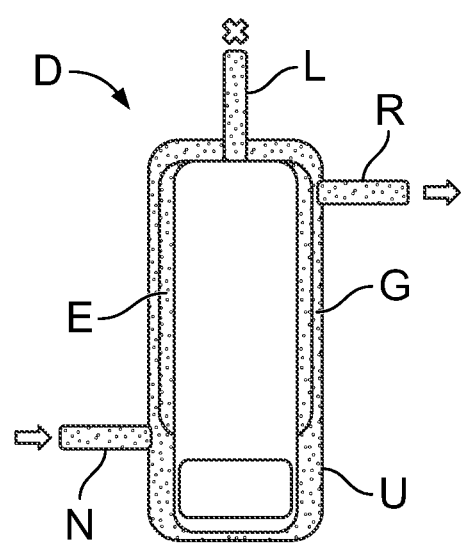
Figure 2A:
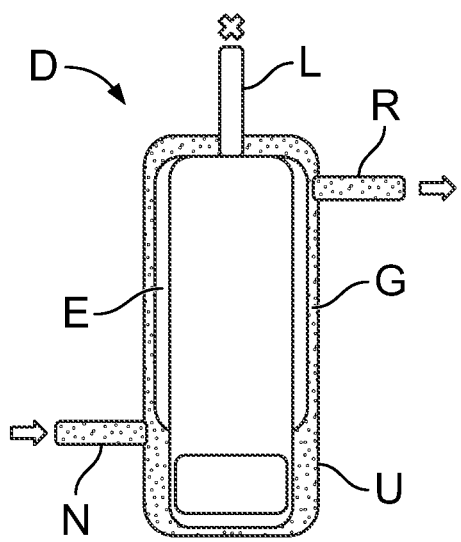
FIGS. 2A-2D illustrate a second conventional approach to priming a spinning membrane separator.
Figure 2B:
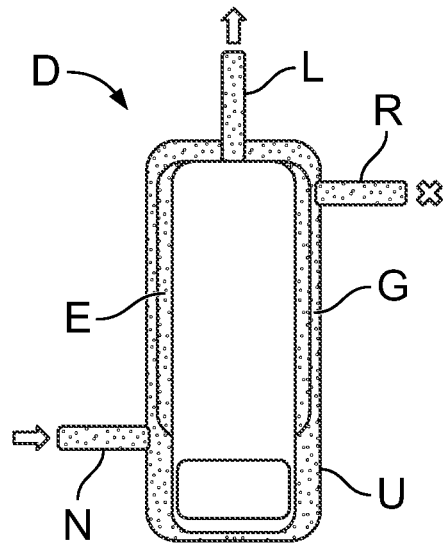
Figure 2C:
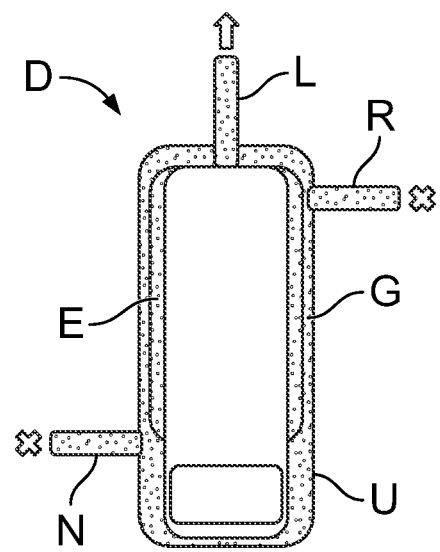
Figure 2D:
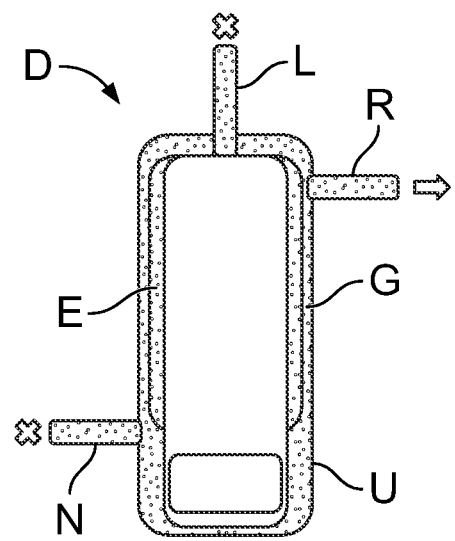
Figure 3:
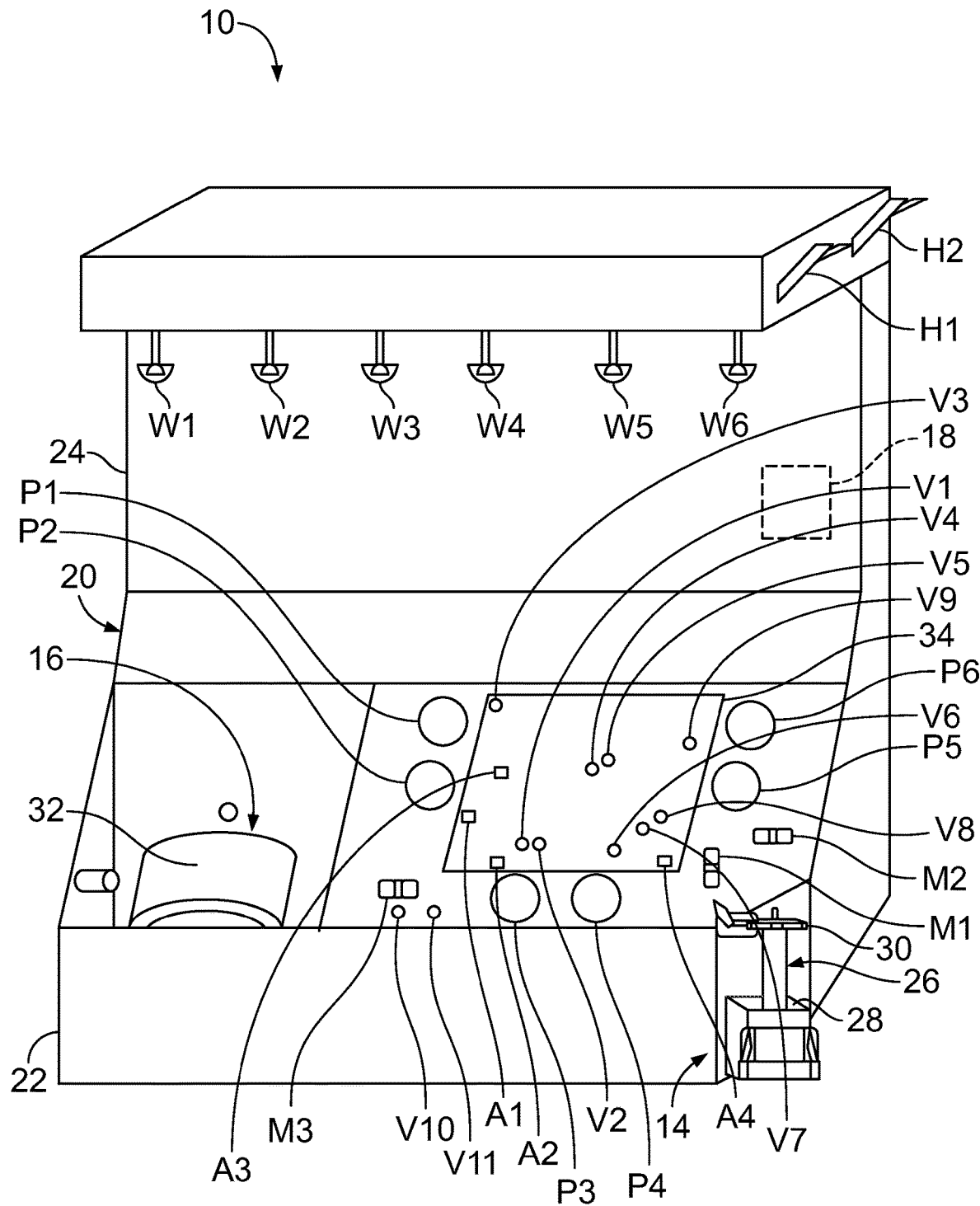
FIG. 3 is a perspective view of an exemplary fluid processing device employing aspects of the present disclosure.
Figure 4:
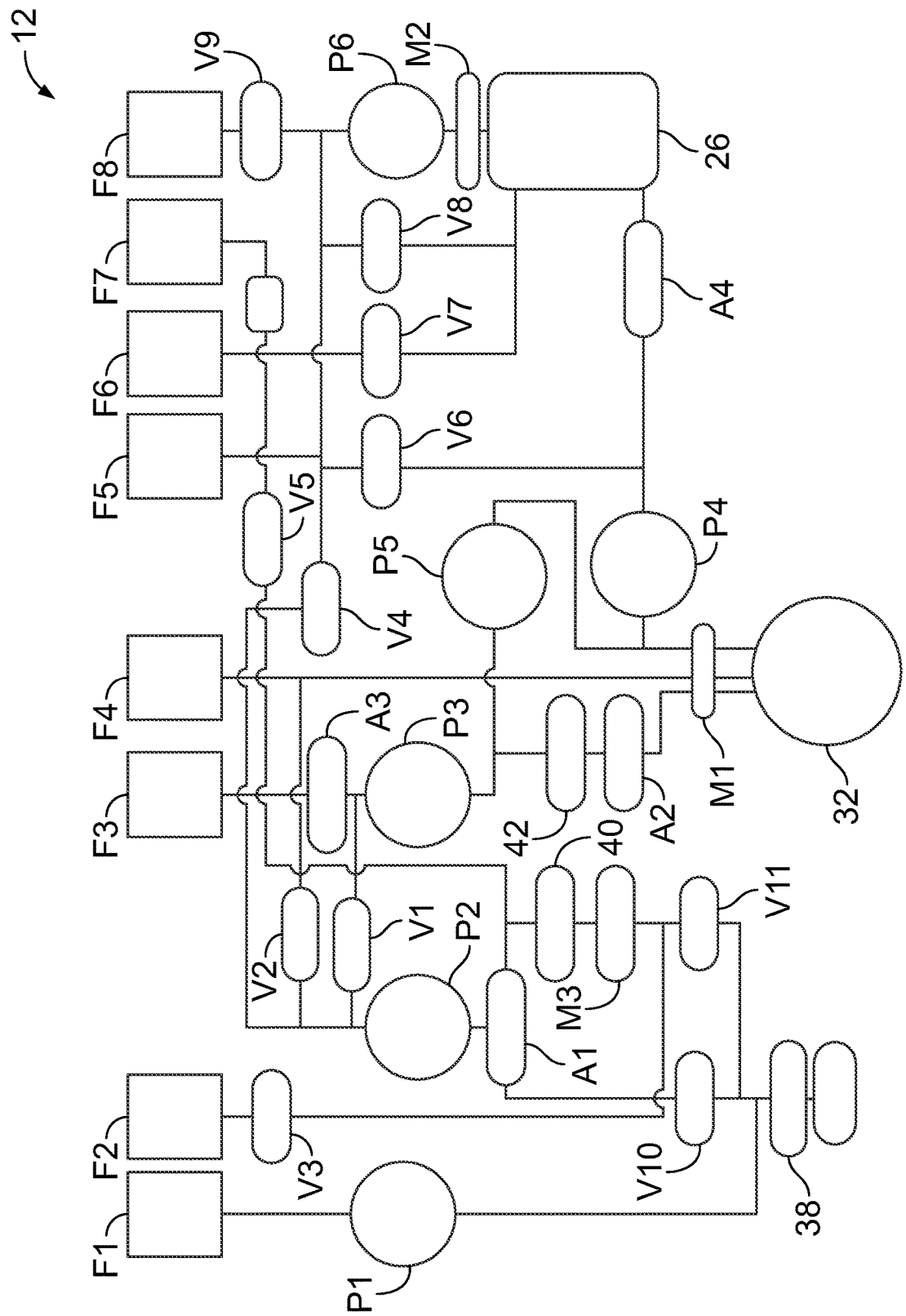
FIG. 4 is a schematic view of an exemplary disposable fluid flow circuit that may be mounted to the fluid processing device of FIG. 3 to complete a fluid processing system according to an aspect of the present disclosure.

Fluid processing systems according to the present disclosure typically include two principal components, a durable and reusable fluid processing device 10 (FIG. 3) and a disposable fluid flow circuit 12 (FIG. 4). The illustrated fluid processing device 10 includes a spinning membrane separator drive unit 14, a centrifuge or centrifugal separator 16, additional components that control fluid flow through the disposable fluid flow circuit 12, and a controller 18 (FIG. 3), which governs the operation of the other components of the fluid processing device 10 to perform a procedure selected by the operator. The principles described herein regarding priming of a spinning membrane separator are not limited to any particular fluid processing systems or procedures, so no complete fluid processing devices or procedures will be described in detail herein. However, reference may be made to POT Patent Application Publication No. WO 2018/053217 A1 for a detailed description of the fluid processing device 10 of FIG. 3, along with various exemplary procedures that may be carried out using such a system.

I. The Durable Fluid Processing Device

The fluid processing device 10 (FIG. 3) is configured as a durable item that is capable of long-term use. It should be understood that the fluid processing device 10 of FIG. 3 is merely exemplary of one possible configuration and that fluid processing devices according to the present disclosure may be differently configured. For example, it is within the scope of the present disclosure for the fluid processing device to omit a centrifugal separator 16, which could include the fluid processing device being configured as a modified version of the device shown and described in U.S. Pat. No. 9,388,383 (e.g., with the device and/or an associated fluid flow circuit being modified to associate pumps with the inlet port and the filtrate outlet port of a spinning membrane separator instead of the inlet port and the retentate outlet port).

The illustrated fluid processing device 10 includes a spinning membrane separator drive unit 14, a centrifuge or centrifugal separator 16, a pump system and various valves that control fluid flow through the disposable fluid flow circuit 12, and assorted other components (e.g., sensors, weight scales, etc.). The fluid processing device 10 also includes a controller 18 that governs the operation of the other components of the fluid processing device 10 to perform a procedure selected by an operator. The controller 18 may be variously configured without departing from the scope of the present disclosure. In one embodiment, the controller 18 may include a microprocessor (which, in fact may include multiple physical and/or virtual processors). According to other embodiments, the controller 18 may include one or more electrical circuits designed to carry out the actions described herein. In fact, the controller 18 may include a microprocessor and other circuits or circuitry. In addition, the controller 18 may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessor to carry out one or more actions as described below.

In the illustrated embodiment, the fluid processing device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24.

A. Spinning Membrane Separator Drive Unit

The illustrated spinning membrane separator drive unit 14 is configured to accommodate a generally cylindrical spinning membrane separator 26 of the fluid flow circuit 12. POT Patent Application Publication No. WO 2018/053217 A1 describes an exemplary spinning membrane separator that would be suitable for incorporation into the fluid flow circuit 12, but it should be understood that the spinning membrane separator and the matching spinning membrane separator drive unit 14 may be differently configured without departing from the scope of the present disclosure.

The spinning membrane separator drive unit 14 may include a base 28 configured to receive a lower portion of the spinning membrane separator 26 and an upper end cap 30 to receive an upper portion of the spinning membrane separator. The upper end cap 30 may be positioned directly above the base 28 to orient a spinning membrane separator 26 received by the spinning membrane separator drive unit 14 vertically and to define a vertical axis about which the spinning membrane separator 26 is spun, as well as aid in maintaining a seal between the annulus and the filtrate outlet port.

The base 28 is configured to spin one or more components of the spinning membrane separator 26 about the axis defined by the spinning membrane separator drive unit 14. The mechanism by which the spinning membrane separator drive unit 14 spins one or more components of the spinning membrane separator 26 may vary without departing from the scope of the present disclosure. In one embodiment, a component of the spinning membrane separator 26 to be spun includes at least one element configured to be acted upon by a magnet (e.g., a metallic material), while the spinning membrane separator drive unit 14 includes one or more magnets (e.g., a series of magnetic coils or semi-circular arcs). By modulating the magnetic field acting upon the aforementioned element of the spinning membrane separator 26, the component or components of the spinning membrane separator 26 may be made to spin in different directions and at varying speeds. In other embodiments, different mechanisms may be employed to spin the component or components of the spinning membrane separator 26.

Regardless of the mechanism by which the spinning membrane separator drive unit 14 spins the component or components of the spinning membrane separator 26, the component or components of the spinning membrane separator 26 is/are preferably spun at a speed that is sufficient to create Taylor vortices in a gap or annulus between the spinning component and a stationary component of the spinning membrane separator 26 (or a component that spins at a different speed). Fluid to be separated within the spinning membrane separator 26 flows through this annulus, and filtration may be dramatically improved by the creation of Taylor vortices.

Typically, a spinning membrane separator drive unit 14 and matching spinning membrane separator 26 are used to separate plasma from cellular blood components. For example, in one embodiment platelet-rich plasma enters an annulus between an outer stationary housing and an internal spinning rotor covered by a porous membrane. The platelet-rich plasma moves along the longitudinal axis of the housing toward an exit region, with plasma passing through the membrane and out of the housing either into a collection bag or back to the blood source. The remaining blood components, which are primarily platelets, move to the exit region between the rotor and the housing and then are conveyed into a collection bag. While it is most common for a spinning membrane separator drive unit 14 and matching spinning membrane separator 26 to be used to separate plasma from other blood components, it is within the scope of the present disclosure for the combination to separate other fluid components and/or to be configured for other fluid processing procedures (e.g., cell washing).

As for the centrifugal separator 16, the principles described herein are specific to priming of a spinning membrane separator received by an associated spinning membrane separator drive unit, so the centrifugal separator 16 is not described in detail herein. However, reference may be made to POT Patent Application Publication No. WO 2018/053217 A1 for a detailed description of an exemplary centrifugal separator 16 (and associated centrifugal separation chamber 32) that is suitable for incorporation into a fluid processing device 10 of the type shown in FIG. 3 and described herein.

B. Other Components of the Fluid Processing Device

In addition to the spinning membrane separator drive unit 14 and the centrifugal separator 16, the fluid processing device 10 may include other components compactly arranged to aid fluid processing.

Figure 5:
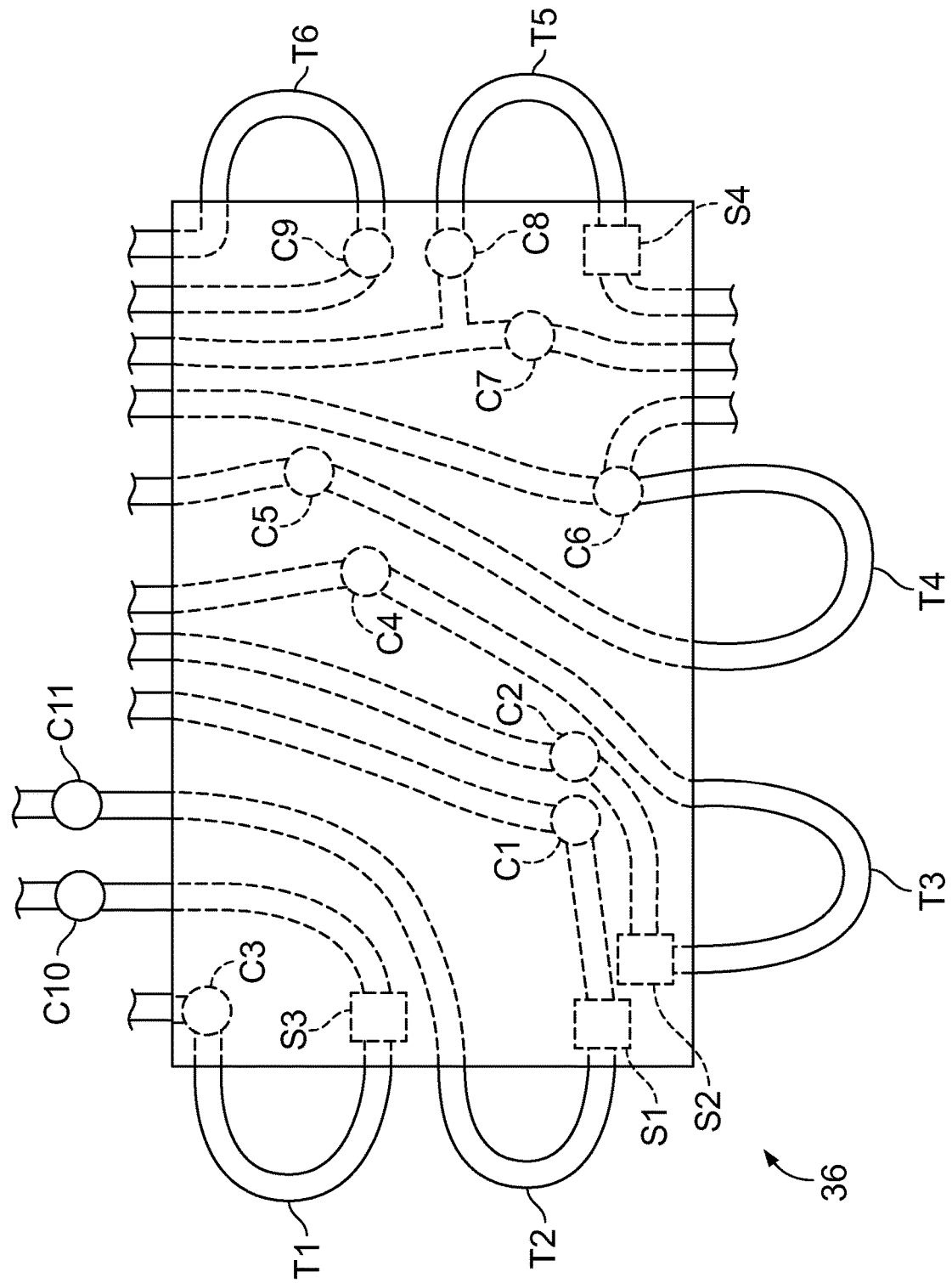
FIG. 5 is a top plan view of an exemplary cassette of a fluid flow circuit, which can be actuated to perform a variety of different fluid processing procedures in association with the fluid processing device shown in FIG. 3.

The generally horizontal portion 22 of the case 20 of the illustrated fluid processing device 10 includes a cassette station 34, which accommodates a cassette 36 of the fluid flow circuit 12 (FIG. 5). In one embodiment, the cassette station 34 is similarly configured to the cassette station of POT Patent Application Publication No. WO 2018/053217 A1. The illustrated cassette station 34 includes a plurality of clamps or valves V1-V9 (FIGS. 3 and 4), which move between a plurality of positions (e.g., between a retracted or lowered position and an actuated or raised position) to selectively contact or otherwise interact with corresponding valve stations C1-C9 of the cassette 36 of the fluid flow circuit 12 (FIG. 5). Depending on the configuration of the fluid flow circuit 12, its cassette 36 may not include a valve station C1-C9 for each valve V1-V9 of the cassette station 34, in which case fewer than all of the valves V1-V9 will be used in a procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 34 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 34 and cassette 36 may be differently configured and operate differently from the valves V10 and V11 and valve stations C10 and C11 that are spaced away from the cassette station 34.

The cassette station 34 may be provided with additional components, such as pressure sensors A1-A4, which interact with sensor stations S1-S4 of the cassette 36 to monitor the pressure at various locations of the fluid flow circuit 12. For example, if the fluid source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifugal separation chamber 32. The controller 18 may receive signals from the pressure sensor A1-A4 that are indicative of the pressure within the fluid flow circuit 12 and, if a signal indicates a low- or high-pressure condition, the controller 18 may initiate an alarm or error condition to alert an operator to the condition and/or to attempt to bring the pressure to an acceptable level without operator intervention.

The fluid processing device 10 may also include a plurality of pumps P1-P6 (which may be collectively referred to as a pump system) to cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696 (which is hereby incorporated by reference herein). Each pump P1-P6 engages a different tubing loop T1-T6 extending from a side surface of the cassette 36 (FIG. 5) and may be selectively operated under command of the controller 18 to cause fluid to flow through a portion of the fluid flow circuit 12. In one embodiment, all or a portion of the cassette station 34 may be capable of translational motion in and out of the case 20 to allow for automatic loading of the tubing loops T1-T6 into the associated pump P1-P6.

The illustrated fluid processing device 10 also includes an optical detection assembly or centrifugal separator sensor M1 for determining one or more properties of fluids flowing out of and/or into the centrifugal separator 16. If the fluid flowing out of the centrifugal separator 16 includes red blood cells, the centrifugal separator sensor M1 may be configured to determine the hematocrit of the fluid. If the fluid flowing out of the centrifugal separator 16 is platelet-rich plasma, the centrifugal separator sensor M1 may be configured to determine the platelet concentration of the platelet-rich plasma. The centrifugal separator sensor M1 may detect the one or more properties of a fluid by optically monitoring the fluid as it flows through tubing of the fluid flow circuit 12 or by any other suitable approach. The controller 18 may receive signals from the centrifugal separator sensor M1 that are indicative of the nature of flow into and out of the centrifuge separator 16 (e.g., whether air or a liquid flow is flowing through an inlet or outlet conduit connected to the centrifugal separation chamber 32, whether fluid is flowing through such conduit or is stagnant, etc.) and use the signals to optimize the separation procedure. If one or more properties of a fluid flowing into or out of the centrifugal separation chamber 32 is outside of an acceptable range, then the controller 18 may initiate an alarm or error condition to alert an operator to the condition. Exemplary optical detection assemblies are described in U.S. Pat. No. 6,419,822 and U.S. Patent Application Publication No. 2019/0369008 (both of which are hereby incorporated herein by reference), but it should be understood that a different approach may also be employed for optically monitoring fluid flow into and out of the centrifugal separator 16.

The illustrated fluid processing device 10 further includes a spinner outlet sensor M2, which accommodates tubing of the fluid flow circuit 12 that flows a filtrate out of the spinning membrane separator 26. The spinner outlet sensor M2 monitors the filtrate to determine one or more properties of the substance, and may do so by optically monitoring the filtrate as it flows through the tubing or by any other suitable approach. In one embodiment, separated plasma flows through the tubing, in which case the spinner outlet sensor M2 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) or by any other suitable device and/or method.

The illustrated fluid processing device 10 also includes an air detector M3 (e.g., an ultrasonic bubble detector), which accommodates tubing of the fluid flow circuit 12 that flows fluid to a recipient. It may be advantageous to prevent air from reaching the recipient, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F8 of the fluid flow circuit 12 (FIG. 4). The containers F1-F8 receive fluid components or waste products separated during processing or other assorted fluids (e.g., priming fluids, intravenous fluids, or additive fluids). Each weight scale W1-W6 transmits to the controller 18 a signal that is indicative of the weight of the fluid within the associated container F1-F8 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 2 or other suitably sized and configured objects.

C. Controller

As described above, the fluid processing device 10 includes a controller 18, which is suitably configured and/or programmed to control operation of the fluid processing device 10. In one embodiment, the controller 18 comprises a main processing unit (MPU), which can comprise, e.g., a Pentium™ type microprocessor made by Intel Corporation, although other types of conventional microprocessors can be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid processing device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedure applications (e.g., plasma exchange, red blood cell exchange, and photopheresis) can be included without departing from the scope of the present disclosure.

More particularly, in carrying out any one of these fluid processing applications, the controller 18 is configured and/or programmed to control one or more of the following tasks: drawing fluid into a fluid flow circuit 12 mounted to the fluid processing device 10, conveying fluid through the fluid flow circuit 12 to a location for separation (i.e., into the spinning membrane separator 26 or the centrifugal separation chamber 32 of the fluid flow circuit 12), separating the fluid into two or more components as desired, and conveying the separated components into storage containers, to a second location for further separation (e.g., into whichever of the spinning membrane separator 26 and centrifugal separation chamber 32 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing a pump to convey fluid through a portion of the fluid flow circuit 12 at a particular flow rate. Hence, while it may be described herein that a particular component of the fluid processing device 10 (e.g., the spinning membrane separator drive unit 14 or the centrifugal separator 16) performs a particular function, it should be understood that that component is being controlled by the controller 18 to perform that function.

Before, during, and after a procedure, the controller 18 may receive signals from various components of the fluid processing device 10 to monitor various aspects of the operation of the fluid processing device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 12 (FIG. 4), it is intended to be a sterile, single use, disposable item. Before beginning a given procedure, the operator loads various components of the fluid flow circuit 12 in the case 20 in association with the fluid processing device 10. The controller 18 implements the procedure based upon preset protocols, taking into account other input from the operator. Upon completing the procedure, the operator removes the fluid flow circuit 12 from association with the fluid processing device 10. The portions of the fluid flow circuit 12 holding the collected fluid component or components (e.g., collection containers or bags) are removed from the case 20 and retained for storage, immediate use, or further processing. The remainder of the fluid flow circuit 12 is removed from the case 20 and discarded.

A variety of different disposable fluid flow circuits may be used in combination with the fluid processing device 10, with the appropriate fluid flow circuit depending on the procedure to be carried out using the system. Generally speaking, though, the fluid flow circuit 12 includes a cassette 36 (FIG. 5) to which the other components of the fluid flow circuit 12 are connected by flexible tubing or conduits. The other components may include a plurality of fluid containers F1-F8 (for holding fluid to be processed, a separated fluid component, a priming fluid, or an additive solution, for example), one or more fluid source access devices (e.g., a connector for accessing fluid within a fluid container), a spinning membrane separator 26 (FIGS. 6 and 7), and (optionally) a centrifugal separation chamber 32.

B. Cassette And Tubing

The cassette 36 (FIG. 5), in combination with the cassette station 34 and the controller 18, provides a centralized, programmable, integrated platform for all the pumping and many of the valving functions required for a given fluid processing procedure. In one embodiment, the cassette 36 is similarly configured to the cassette of POT Patent Application Publication No. WO 2018/053217 A1.

In use, the cassette 36 is mounted to the cassette station 34 of the fluid processing device 10, with a flexible diaphragm of the cassette 36 placed into contact with the cassette station 34. The flexible diaphragm overlays an array of interior cavities formed by the body of the cassette 36. The different interior cavities define sensor stations S1-S4, valve stations C1-C9, and a plurality of flow paths or conduits. The side of the cassette 36 opposite the flexible diaphragm may be sealed by another flexible diaphragm or a rigid cover, thereby sealing fluid flow through the cassette 36 from the outside environment.

Each sensor station S1-S4 is aligned with an associated pressure sensor A1-A4 of the cassette station 34, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 36 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 36. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 36 to interact with pumps P1-P6 of the fluid processing device 10. In the illustrated embodiment, six tubing loops T1-T6 extend from the cassette 36 to be received by a different one of six pumps P1-P6, but in other embodiments, a procedure may not require use of all of the pumps P1-P6, in which case the cassette 36 may include fewer than six tubing loops. The different pumps P1-P6 may interact with the tubing loops T1-T6 of the cassette 36 to perform different tasks during a procedure. Certain procedures require fewer than all of the sensor stations, valve stations, and/or tubing loops illustrated in the exemplary cassette 36 of FIG. 5, such that it should be understood that the cassettes of different fluid flow circuits 12 may be differently configured (e.g., with fewer sensor stations, valve stations, and/or tubing loops) without departing from the scope of the present disclosure.

Additional tubing or conduits extend from the side surface of the cassette 36 to connect to the other components of the fluid flow circuit 12, such as the various fluid containers F1-F8, the spinning membrane separator 26, and the centrifugal separation chamber 32. The tubing connected to the centrifugal separation chamber 32 (which includes one inlet conduit and two outlet conduits) may be aggregated into an umbilicus that is engaged by a yoke member of the centrifugal separator 16 to cause the umbilicus to orbit around and spin or rotate the centrifugal separation chamber 32 (if provided) during a procedure.

Various additional components may be incorporated into the tubing leading out of the cassette 36 or into one of the cavities of the cassette 36. For example, as shown in FIG. 4, a manual clamp 38 may be associated with a line or lines leading to the fluid source and/or fluid recipient, a return line filter 40 (e.g., a microaggregate filter) may be associated with a line leading to a fluid recipient, filters may be positioned upstream of one or more of the fluid containers to remove a substance (e.g., leukocytes) from a separated component (e.g., red blood cells) flowing into the fluid container, and/or an air trap 42 may be positioned on a line upstream of the centrifugal separation chamber 32.

C. Spinning Membrane Separator

Turning now to FIGS. 6 and 7, an exemplary spinning membrane separator 26 is shown. The spinning membrane separator 26 is associated with the remainder of the fluid flow circuit 12 by an inlet port 44 and two outlet ports 46 and 48. The inlet port 44 is shown as being associated with a bottom end or portion of the spinning membrane separator 26, while the outlet ports 46 and 48 are associated with an upper end or portion of the spinning membrane separator 26.

The illustrated spinning membrane separator 26 includes a generally cylindrical housing 50 mounted concentrically about a longitudinal vertical central axis. An internal member or rotor 52 is mounted concentrically with the central axis. The housing 50 and rotor 52 are relatively rotatable, as described above with respect to the spinning membrane separator drive unit 14. In a preferred embodiment, the housing 50 is stationary and the rotor 52 is a rotating spinner that is rotatable concentrically within the cylindrical housing 50. In such an embodiment, the housing 50 (or at least its upper and lower ends) are formed of non-magnetic material, while the rotor 52 includes an element (e.g., a metallic material) that interacts with a magnet of the spinning membrane separator drive unit 14 to rotate the rotor 52 within the housing 50, as described above.

The boundaries of the fluid flow path are generally defined by the gap or annulus 54 between the interior surface of the housing 50 and the exterior surface of the rotor 52 covered by a membrane, which is sometimes referred to as the shear gap. A typical annulus 54 may be approximately 0.025-0.050 inches (0.067-0.127 cm) and may be of a uniform dimension along the axis, for example, where the axis of the housing 50 and rotor 52 are coincident. Alternatively, the width of the annulus 54 also may vary along the axial direction, for example with the width of the annulus 54 increasing in the direction of flow to limit hemolysis when a red blood cell-containing fluid is conveyed into the spinning membrane separator 26. Such an annulus width may range from about 0.025 to about 0.075 inches (0.06-0.19 cm). For example, in one embodiment, the axes of the housing 50 and rotor 52 are coincident, with the outer diameter of the rotor 52 decreasing in the direction of flow, while the inner diameter of the housing 50 remaining constant. In other embodiments, the inner diameter of the housing 50 may increase while the outer rotor diameter remains constant or both surfaces may vary in diameter. In one exemplary embodiment, the annulus width may be about 0.035 inches (0.088 cm) at the upstream or inlet end of the annulus 54 and about 0.059 inches (0.15 cm) at the downstream end or terminus of the annulus 54. The annulus width could change linearly or stepwise or in some other manner as may be desired. In any event, the width dimension of the annulus 54 is preferably selected so that at the desired relative rotational speed, Taylor-Couette flow, such as Taylor vortices, are created in the annulus 54 and (in the case of a red blood cell-containing fluid being processed) hemolysis is limited.

A fluid to be processed is fed into the annulus 54 by the inlet port 44 (FIG. 6), which directs the fluid into the fluid flow entrance region at or adjacent to the bottom end of the spinning membrane separator 26. The spinning membrane separator drive unit 14 causes rotation of the rotor 52 within the housing 50, creating Taylor vortices within the annulus 54.

The outer surface of the rotor 52 is at least partially (and more preferably, substantially or entirely) covered by a porous membrane 56. The membrane 56 has a nominal pore size that may vary, depending on the nature of the substances to be removed. For example, if only a supernatant is to be filtered out during cell washing of a mononuclear cell product, then a nominal pore size of 0.65-0.8 microns may be employed. In another example, in which supernatant, platelets, and some smaller red blood cells are to be filtered out, a nominal pore size of 4.0 microns may be advantageous. In yet another example, to limit fouling of the membrane 56 due to build-up of protein aggregates, a nominal pore size of up to 1.3 microns may be employed without losing cellular components to the filtrate. It should be understood that these are only exemplary and that membranes having other pore sizes may alternatively be used without departing from the scope of the present disclosure. Membranes useful in the methods described herein may be fibrous mesh membranes (in which case, the membrane will have an "effective pore size," rather than a defined pore size), cast membranes, track-etched membranes or other types of membranes that will be known to those of skill in the art. For example, in one embodiment, the membrane 56 may have a polyester mesh (substrate) with nylon particles solidified thereon, thereby creating a tortuous path through which only certain sized components will pass. In another embodiment, the membrane 56 may be made of a thin (approximately 15 micron thick) sheet of, for example, polycarbonate with pores or holes defined therein that are sized and configured to allow passage of only a selected one or more fluid components.

In the illustrated embodiment, the outer surface of the rotor 52 is shaped to define a series of spaced-apart circumferential grooves or ribs 58 separated by annular lands 60 (FIG. 7). The surface channels defined by the circumferential grooves 58 are interconnected by longitudinal grooves 62. At one or both ends of the rotor 52, these grooves 58 are in communication with a central orifice or manifold 64. Pumping fluid into and out of the spinning membrane separator 26 causes the substance being filtered out (which is referred to herein as a filtrate) to flow through the membrane 56 and grooves 58 (into the interior of the rotor 52), while the while remainder of the fluid (which is referred to herein as a retentate) remains within the annulus 54 as fluid flows from the inlet port 44 at the bottom portion of the spinning membrane separator 26 toward the upper portion. Relative rotation of the rotor 52 and housing 50 causes a particular flow pattern within the annulus 54 (described above) that enables filtration without clogging the membrane 56.

At the upper portion of the spinning membrane separator 26, the filtrate within the interior of the rotor 52 exits the spinning membrane separator 26 via an upper or filtrate outlet port 46 that is concentric with the rotational axis and in fluid communication with the central orifice 64 or interior of the rotor 52 (FIG. 7), with the substance flowing into a line associated with the filtrate outlet port 46. The remainder of the fluid (or retentate) within the annulus 54 exits the annulus 54 via a side or retentate outlet port 48 positioned adjacent to the upper end or portion of the housing 50 and oriented generally tangentially to the annulus 54 (FIG. 6), flowing into a line associated with the retentate outlet port 48.

III. Priming of Spinning Membrane Separator

Depending on the fluid processing objectives, there is a suitable procedure for separating or otherwise processing any of a variety of different fluids. Accordingly, prior to processing, an operator selects the desired protocol (e.g., using an operator interface station, if provided), which informs the controller 18 of the manner in which it is to control the other components of the fluid processing device 10 during the procedure.

The operator may also proceed to enter various parameters. In the case of blood separation or processing, this may include information regarding the blood source, along with the target yield for the various blood components (which may also include entering a characteristic of the blood, such as a platelet pre-count) or some other collection control system (e.g., the amount of whole blood to be processed).

If there are any fluid containers (e.g., a storage solution container) that are not integrally formed with the fluid flow circuit 12, they may be connected to the fluid flow circuit 12 (e.g., by piercing a septum of a tube of the fluid flow circuit 12 or via a luer connector), with the fluid flow circuit 12 then being mounted to the fluid processing device 10 (including the fluid containers F1-F8 being hung from the weight scales W1-W6 and the hooks or supports H1 and H2, as appropriate). An integrity check of the fluid flow circuit 12 may be executed by the controller 18 to ensure the various components are properly connected and functioning.

Following a successful integrity check, the fluid flow circuit 12 is primed to move air contained in the various conduits and in the spinning membrane separator 26 into a more suitable location (e.g., a waste container). In the case of blood separation or processing, saline or anticoagulant may be suitable priming fluids, though it should be understood that the priming principles described herein are not limited to use with any particular priming fluid.

A. First Stage

Figure 8:
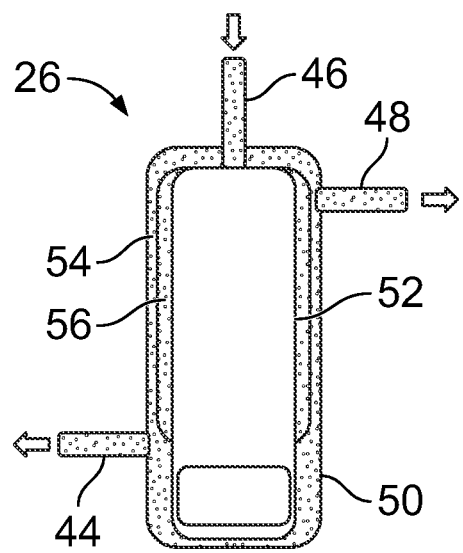
FIG. 8 is a schematic view of the fluid flow path through the spinning membrane separator of FIGS. 6 and 7 during a first stage of a priming procedure.

In the first stage of an exemplary priming procedure (which is shown in FIG. 8), a priming fluid is conveyed into the spinning membrane separator 26 via the filtrate outlet port 46 and out of the spinning membrane separator 26 (along with air) via the inlet port 44 and the retentate outlet port 48. This direction of flow is opposite to the typical direction of flow through the spinning membrane separator 26 (in which fluid enters the spinning membrane separator 26 via the inlet port 44, with portions of the fluid exiting via the filtrate outlet port 46 and the retentate outlet port 48) and different from any of the stages of the conventional priming procedures illustrated in FIGS. 1A-2D. Conveying priming fluid into the spinning membrane separator 26 via the filtrate outlet port 46 pushes air from the interior of the rotor 52 through the membrane 56 and into the annulus 54.

The first stage may be variously executed without departing from the scope of the present disclosure. In an exemplary embodiment, the spinning membrane separator drive unit 14 is controlled by the controller 18 to rotate the rotor 52 within the housing 50 during the first stage, which uses centripetal force to help push air out from behind the membrane 56 into the annulus 54. The rotor 52 may be rotated at any rate without departing from the scope of the present disclosure, with the rotor 52 being rotated at a rate of approximately 600 rpm in an exemplary embodiment.

The controller 18 controls one or more of the pumps P1-P6 of the pump system to convey priming fluid from a source (e.g., one of the containers F1-F8 of the fluid flow circuit 12), through a portion of the fluid flow circuit 12, and into the spinning membrane separator 26 via the filtrate outlet port 46. In an exemplary embodiment, pump P6 (which may be associated with a conduit connected to the filtrate outlet port 46, as shown in FIG. 4) operates to convey priming fluid to the filtrate outlet port 46, but any other pump or combination of pumps may be employed without departing from the scope of the present disclosure. The controller 18 may control the pump system to convey the priming fluid into the spinning membrane separator 26 at any rate without departing from the scope of the present disclosure, with the priming fluid being conveyed into the spinning membrane separator 26 at a rate of approximately 30 ml/min in an exemplary embodiment.

If pumps are associated with the inlet port 44 and the retentate outlet port 48, the controller 18 may control one or both of them to operate to convey the priming fluid out of the spinning membrane separator 26. In the illustrated embodiment, pump P4 of the pump system is associated with the inlet port 44, while there is no pump associated with the retentate outlet port 48. In this case, the flow rate of fluid through the retentate outlet port 48 is equal to the difference between the operational rates of the pumps associated with the inlet port 44 and the filtrate outlet port 46. For example, in an exemplary embodiment, fluid is pumped into the spinning membrane separator 26 via the filtrate outlet port 46 at a rate of approximately 30 ml/min (as noted above), while fluid is pumped out of the spinning membrane separator 26 via the inlet port 44 at a rate of approximately 10 ml/min. In this example, fluid will be forced out of the retentate outlet port 48 at a rate of approximately 20 ml/min (i.e., 30 ml/min-10 ml/min), which may be advantageous in removing air from the annulus 54. While more fluid is conveyed out of the spinning membrane separator 26 via the retentate outlet port 48 than via the inlet port 44 in this example, it should be understood that it is within the scope of the present disclosure for more fluid to instead be conveyed out of the spinning membrane separator 26 via the inlet port 44 or for fluid to exit the spinning membrane separator 26 via the inlet port 44 and the retentate outlet port 48 at the same rates. In general, due to aft floating, it may be advantageous for more fluid to exit the spinning membrane separator 26 via whichever of the inlet port 44 and the retentate outlet port 48 is positioned at a greater elevation. Thus, if the spinning membrane separator 26 were configured with the inlet port 44 positioned at a greater elevation than the retentate outlet port 46, then it may be advantageous for more fluid to exit the spinning membrane separator 26 via the inlet port 44 than the retentate outlet port 46 during the first stage.

The fluid and air exiting the spinning membrane separator 26 via the inlet port 44 and the retentate outlet port 48 may be directed to any suitable location within the fluid flow circuit 12. In one embodiment, the priming fluid exiting the spinning membrane separator 26 via the inlet port 44 is directed back into the priming fluid source (i.e., the inlet port 44 and the filtrate outlet port 46 are in fluid communication with the same fluid source or reservoir, such as a priming fluid bag), while the priming fluid exiting the spinning membrane separator 26 via the retentate outlet port 48 is directed to a separate bag or container (e.g., one of containers F1-F8, which may be treated as a waste container). By such an arrangement, the priming fluid exiting the spinning membrane separator 26 via the inlet port 44 is used to partially restock the priming fluid source or reservoir or to prime additional lines of the fluid flow circuit 12, rather than that fluid going to waste. Additionally, as will be described in greater detail, priming fluid may be conveyed into the spinning membrane separator 26 via the inlet port 44 during an option second stage of the priming procedure, such that placing the inlet port 44 in fluid communication with a fluid source or reservoir is advantageous. However, it should be understood that such an arrangement is merely exemplary and that fluid and air exiting the spinning membrane separator 26 during the first stage of the priming procedure may be directed elsewhere without departing from the scope of the present disclosure.

The first stage of the priming procedure may be ended (by stopping the flow of priming fluid into the spinning membrane separator 26) at any time and based upon any criteria. In an exemplary embodiment, the priming fluid and air exiting the spinning membrane separator 26 via the retentate outlet port 48 is directed into a container associated with one of the weight scales W1-W6. This container is initially empty at the beginning of the procedure, such that the change in weight of the container during the course of the first stage of the priming procedure is indicative of the volume of fluid that has exited the spinning membrane separator 26 via the retentate outlet port 48. In such an embodiment, the controller 18 may be configured to control the pump system to stop conveying fluid into the spinning membrane separator 26 via the filtrate outlet port 46 (i.e., to end the first stage of the priming procedure) based at least in part upon a change in weight registered by the weight scale associated with the container that receives the priming fluid and air exiting the spinning membrane separator 26 via the retentate outlet port 48. For example, in an exemplary embodiment, the controller 18 is configured to end the first stage of the priming procedure when the weight scale associated with the container that receives the priming fluid and air exiting the spinning membrane separator 26 via the retentate outlet port 48 registers an increase in weight of 30 grams. If this approach is followed, it may be advantageous to base the target change in weight on the volume of the spinning membrane separator 26 and/or the dimensions of the membrane 56 to ensure that substantially all of the air behind the membrane 56 is pushed into the annulus 54.

In other embodiments, other criteria may be used to determine when to end the first stage of the priming procedure. For example, the first stage may be ended upon a target volume of priming fluid being conveyed into the spinning membrane separator 26 via the filtrate outlet port 46 (which may be determined based upon the operational rate of the pump associated with the filtrate outlet port 46). In another embodiment, the first stage may be ended based upon a signal from an assembly monitoring flow through a conduit associated with the inlet port 44 or the retentate outlet port 48. For example, the controller 18 may be configured to end the first stage of the priming procedure when it is determined that air is no longer exiting one or both of the inlet port 44 and the retentate outlet port 48.

In any case, when the controller 18 has determined that it is appropriate to end the first stage of the priming procedure, it commands all of the pumps of the pump system to cease operation. If the spinning membrane separator drive unit 14 is operating to rotate the rotor 52 within the housing 50 of the spinning membrane separator 26, it may be advantageous for the controller 18 to allow the rotor 52 to continue spinning.

B. Second Stage

Figure 9:
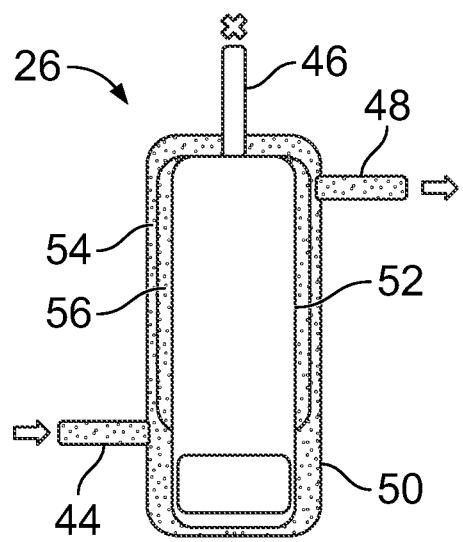
FIG. 9 is a schematic view of the fluid flow path through the spinning membrane separator of FIGS. 6 and 7 during an optional second stage of a priming procedure.

At the end of the first stage, some of the air from the interior of the rotor 52 that has been pushed through the membrane 56 and into the annulus 54 may remain in the annulus 54. The residual air may be cleared from the annulus 54 during fluid processing or may instead by cleared prior to fluid processing during an optional second priming stage. During the optional second priming stage, priming fluid is conveyed into the spinning membrane separator 26 via the inlet port 44 and out of the spinning membrane separator 26 (along with any residual air) via the retentate outlet port 48 in a second stage of the exemplary priming procedure (which is shown in FIG. 9). Flow through the filtrate outlet port 46 may be prevented (as shown in FIG. 9) by any suitable approach (e.g., by clamping or otherwise closing a conduit connected to the filtrate outlet port 46 and/or ceasing operation of a pump associated with the filtrate outlet port 46) to better ensure that the priming fluid flows through only the annulus 54 (rather than through the membrane 56) to force the residual air out of the spinning membrane separator 26 via the retentate outlet port 48, rather than pushing the air back through the membrane 56. It has been found that such a priming procedure is capable of consistently removing over 95% of the air trapped behind the membrane 56 between the ribs 58 of the rotor 52, compared to conventional approaches, which may be capable of removing only up to approximately 90% of the air between the rotor and the membrane.

The second stage may be variously executed without departing from the scope of the present disclosure. In an exemplary embodiment, the spinning membrane separator drive unit 14 continues to be controlled by the controller 18 to rotate the rotor 52 within the housing 50, which may include the rotor 52 being spun at the same speed at which it was spun during the first stage. Spinning the rotor 52 uses centripetal force to help push air out from behind the membrane 56 into the annulus 54 during the first stage of the priming procedure (as noted above), while helping to retain the air in the annulus 54 (rather than allowing it to pass through the membrane 56) in the second stage. The rotor 52 may be rotated at any rate without departing from the scope of the present disclosure, with the rotor 52 being rotated at a rate of approximately 600 rpm (as in the first stage) in an exemplary embodiment.

The controller 18 controls one or more of the pumps P1-P6 of the pump system to convey priming fluid from a source (e.g., one of the containers F1-F8 of the fluid flow circuit 12), through a portion of the fluid flow circuit 12, and into the spinning membrane separator 26 via the inlet port 44. In an exemplary embodiment, pump P4 (which may be associated with a conduit upstream of the inlet port 44, as shown in FIG. 4) operates to convey priming fluid to the inlet port 44, but any other pump or combination of pumps may be employed without departing from the scope of the present disclosure. The same fluid source may be used in both the first and second stages of the priming procedure (with the inlet port 44 and the filtrate outlet port 46 both fluidly connected to the fluid source, as described above) or priming fluid may instead be drawn from different sources during the two stages, which may be preferred if different priming fluids are to be used during the two stages.

The controller 18 may control the pump system to convey the priming fluid into the spinning membrane separator 26 at any rate without departing from the scope of the present disclosure, with the priming fluid being conveyed into the spinning membrane separator 26 at a rate of approximately 15 ml/min in an exemplary embodiment. In this exemplary embodiment, priming fluid is pumped into the spinning membrane separator 26 during the second stage at a rate that is half of the rate at which it is pumped into the spinning membrane separator 26 during the first stage. This (or some other rate that is lower than the inflow rate during the first stage) may be suitable, on account of less fluid and force being required to clear the air from the annulus 54 (during the second stage) than to force the air from behind the membrane 56 (during the first stage).

If pumps are associated with both the inlet port 44 and the retentate outlet port 48, the controller 18 may control them to operate so as to convey all of the priming fluid entering the spinning membrane separator 26 via the inlet port 44 out of the spinning membrane separator 26 via the retentate outlet port 48. As noted above, in the illustrated embodiment, pump P4 of the pump system is associated with the inlet port 44, while there is no pump associated with the retentate outlet port 48. In this case, the flow rate of fluid through the retentate outlet port 48 is equal to the operational rate of the pump associated with the inlet port 44 (on account of no fluid flowing through the filtrate outlet port 46). Thus, in an exemplary embodiment, priming fluid is pumped into the spinning membrane separator 26 via the inlet port 44 at a rate of approximately 15 ml/min (as noted above), with all of the fluid (along with residual air) being forced out of the retentate outlet port 48 at the same rate.

The fluid and air exiting the spinning membrane separator 26 via the retentate outlet port 48 may be directed to any suitable location within the fluid flow circuit 12. This may include the priming fluid exiting the spinning membrane separator 26 via the retentate outlet port 48 being directed to the same destination as in the first stage or to a different location.

While fluid flow from the inlet port 44 to the retentate outlet port 48 is described above, it should be understood that this flow path may be reversed, with priming fluid instead entering the spinning membrane separator 26 via the retentate outlet port 48 and exiting the spinning membrane separator 26 via the inlet port 44. While this is also effective in clearing air from the annulus 54, it may be advantageous for fluid to instead flow from the inlet port 44 to the retentate outlet port 48 (as shown in FIG. 9), due to there being less resistance to air flow in such a direction (on account of the retentate outlet port 48 being positioned at a higher elevation than the inlet port 44, with air naturally rising from a lower elevation to a higher elevation).

In any event, the second stage of the priming procedure may be ended (by stopping the flow of priming fluid into the spinning membrane separator 26) at any time and based upon any criteria. In an exemplary embodiment, the priming fluid and air exiting the spinning membrane separator 26 via the retentate outlet port 48 is directed into the same container as in the first stage. As described above, this container is associated with one of the weight scales W1-W6, such that the change in weight of the container during the course of the second stage of the priming procedure may be monitored by the controller 18. In such an embodiment, the controller 18 may be configured to control the pump system to stop conveying fluid into the spinning membrane separator 26 (i.e., to end the second stage of the priming procedure) based at least in part upon a change in weight registered by the weight scale associated with the container that receives the priming fluid and air exiting the spinning membrane separator 26 via the retentate outlet port 48. For example, in an exemplary embodiment, the controller 18 is configured to end the second stage of the priming procedure when the weight scale associated with the container that receives the priming fluid and air exiting the spinning membrane separator 26 via the retentate outlet port 48 registers an increase in weight of 30 grams. While this is the same weight change that is used to determine when to end the first stage in the exemplary embodiment, it should be understood that any other change in weight may be selected without departing from the scope of the present disclosure. However, if this approach is employed, it may be advantageous to base the target change in weight on the volume of the spinning membrane separator 26 and/or the dimensions of the annulus 54 and the membrane 56 and any additional fluid flow path volume to ensure that substantially all of the air retained in the annulus 54 at the end of the first stage is pushed out of the spinning membrane separator 26 during the second stage.

In other embodiments, other criteria may be used to determine when to end the second stage of the priming procedure. In accordance with the above description of the first stage, the second stage may be ended upon a target volume of priming fluid being conveyed into the spinning membrane separator 26 via the inlet port 44 (which may be determined based upon the operational rate of the pump associated with the inlet port 44). In another embodiment, the second stage may be ended based upon a signal from an assembly monitoring flow through a conduit associated with the retentate outlet port 48. For example, the controller 18 may be configured to end the second stage of the priming procedure when it is determined that air is no longer exiting the spinning membrane separator 26 via the retentate outlet port 48.

In any case, when the controller 18 has determined that it is appropriate to end the second stage of the priming procedure, it may proceed with any of a number of possible subsequent commands. For example, in the case of a blood separation or processing procedure, the controller 18 may command all of the pumps of the pump system to cease operation while the blood source is connected to the fluid flow circuit 12. When the blood source has been connected to the fluid flow circuit 12, the controller 18 may proceed with a blood separation or processing procedure. Direct interaction between blood cells and the membrane 56 prior to wetting the membrane 56 may cause damage to the cells, such that a more completely wetted or primed membrane 56 resulting from the priming procedure described herein will lead to less cell damage than the membrane of a spinning membrane separator that is primed according to a conventional approach. However, while the techniques described herein are particularly advantageous for use with spinning membrane separators configured for separation or processing of blood or blood components (e.g., separation of platelet-rich plasma into platelet-poor plasma and platelet concentrate), it is again emphasized that the priming principles described herein are applicable to spinning membrane separators configured for use in separating and/or processing any fluid.

Aspects

Aspect 1. A fluid processing device, comprising: a controller; a spinning membrane separator drive unit configured to receive a spinning membrane separator including a housing, a rotor rotatably received within the housing, an inlet port, a filtrate outlet port in fluid communication with an interior of the rotor, and a retentate outlet port in fluid communication with an annulus defined between the housing and the rotor; and a pump system, wherein the controller is configured to execute a priming procedure including controlling the pump system during a first stage to convey a priming fluid into the spinning membrane separator via the filtrate outlet port so as to convey air out of the spinning membrane separator via the inlet port and the retentate outlet port, and then controlling the pump system to stop conveying the priming fluid into the spinning membrane separator via the filtrate outlet port.

Aspect 2. The fluid processing device of Aspect 1, wherein the controller is further configured to, after controlling the pump system to stop conveying the priming fluid into the spinning membrane separator via the filtrate outlet port, control the pump system during a second stage to convey the priming fluid into the spinning membrane separator via the inlet port so as to convey air out of the spinning membrane separator via the retentate outlet port.

Aspect 3. The fluid processing device of Aspect 2, wherein the controller is configured to control the pump system to prevent flow out of the spinning membrane separator via the filtrate outlet port during the second stage.

Aspect 4. The fluid processing device of any one of the preceding Aspects, further comprising a weight scale, wherein the controller is configured to control the pump system to stop conveying the priming fluid into the spinning membrane separator via the filtrate outlet port based at least in part upon a signal received by the controller from the weight scale.

Aspect 5. The fluid processing device of Aspect 4, wherein the weight scale is configured to measure the weight of priming fluid conveyed out of the spinning membrane separator via the retentate outlet port during the first stage.

Aspect 6. The fluid processing device of any one of the preceding Aspects, wherein the pump system includes a first pump associated with the inlet port and a second pump associated with the filtrate outlet port, and the rate of flow through the retentate outlet port is equal to the difference between the operational rates of the first and second pumps.

Aspect 7. The fluid processing device of Aspect 6, wherein the controller is configured to, after controlling the pump system to stop conveying the priming fluid into the spinning membrane separator via the filtrate outlet port, control the first pump during a second stage to convey the priming fluid into the spinning membrane separator via the inlet port so as to convey air out of the spinning membrane separator via the retentate outlet port the first pump to operate at a first operational rate during the first stage, the controller being further configured to control the first pump to operate at a second operational rate during the second stage, with the first and second operational rates being different.

Aspect 8. The fluid processing device of Aspect 7, wherein the second operational rate is greater than the first operational rate.

Aspect 9. The fluid processing device of any one of Aspects 7-8, wherein the controller is configured to control the second pump to operate at a third operational rate during the first stage, and the third operational rate is greater than the second operational rate.

Aspect 10. The fluid processing device of any one of Aspects 2-9, wherein the controller is configured to control the spinning membrane separator drive unit to rotate the rotor within the housing during the first and second stages.

Aspect 11. The fluid processing device of any one of Aspects 2-10, wherein the controller is configured to control the spinning membrane separator drive unit to rotate the rotor within the housing at the same rotational rate during the first and second stages.

Aspect 12. A method of priming a spinning membrane separator including a housing, a rotor rotatably received within the housing, an inlet port, a filtrate outlet port in fluid communication with an interior of the rotor, and a retentate outlet port in fluid communication with an annulus defined between the housing and the rotor, the method comprising: conveying a priming fluid into the spinning membrane separator via the filtrate outlet port during a first stage so as to convey air out of the spinning membrane separator via the inlet port and the retentate outlet port and then ending the first stage.

Aspect 13. The method of Aspect 12, further comprising, after ending the first stage, conveying the priming fluid into the spinning membrane via the inlet port during a second stage so as to convey air out of the spinning membrane separator via the retentate outlet port.

Aspect 14. The method of Aspect 13, wherein How out of the spinning membrane separator via the filtrate outlet port is prevented during the second stage.

Aspect 15. The method of any one of Aspects 12-14, wherein the first stage is ended based at least in part on a volume of priming fluid conveyed out of the spinning membrane separator via the retentate outlet port during the first stage.

Aspect 16. The method of any one of Aspects 12-15, wherein the priming fluid is pumped into the spinning membrane separator via the filtrate outlet port and pumped out of the spinning membrane separator via the inlet port during the first stage, and the rate of flow through the retentate outlet port during the first stage is equal to the difference between the rate at which the priming fluid is pumped into the spinning membrane separator via the filtrate outlet port and the rate at which the priming fluid is pumped out of the spinning membrane separator via the inlet port.

Aspect 17. The method of Aspect 16, wherein the priming fluid is pumped out of the spinning membrane separator via the inlet port at a greater rate than the rate of flow through the retentate outlet port during the first stage.

Aspect 18. The method of any one of Aspects 16-17, further comprising, after ending the first stage, pumping the priming fluid into the spinning membrane via the inlet port during a second stage so as to convey air out of the spinning membrane separator via the retentate outlet port, wherein the priming fluid is pumped out of the spinning membrane separator via the inlet port during the first stage at a rate that is different from the rate at which the priming fluid is pumped into the spinning membrane separator via the inlet port during the second stage.

Aspect 19. The method of Aspect 18, wherein the rate at which the priming fluid is pumped into the spinning membrane separator via the inlet port during the second stage is greater than the rate at which the priming fluid is pumped out of the spinning membrane separator via the inlet port during the first stage.

Aspect 20. The method of any one of Aspects 18-19, wherein the rate at which the priming fluid is pumped into the spinning membrane separator via the filtrate outlet port during the first stage is greater than the rate at which the priming fluid is pumped into the spinning membrane separator via the inlet port during the second stage.

Aspect 21. The method of any one of Aspects 13-20, further comprising rotating the rotor within the housing during the first and second stages.

Aspect 22. The method of Aspect 21, wherein the rotor is rotated within the housing at the same rotational rate during the first and second stages.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing device, comprising:
a controller;
a spinning membrane separator drive unit configured to receive a spinning membrane separator including a housing, a rotor rotatably received within the housing, an inlet port, a filtrate outlet port in fluid communication with an interior of the rotor, and a retentate outlet port in fluid communication with an annulus defined between the housing and the rotor; and
a pump system, wherein the controller is programmed to execute a priming procedure including
controlling the pump system during a first stage to convey a priming fluid into the spinning membrane separator via the filtrate outlet port so as to convey air out of the spinning membrane separator via the inlet port and the retentate outlet port,
controlling the pump system to stop conveying the priming fluid into the spinning membrane separator via the filtrate outlet port, and
after controlling the pump system to stop conveying the priming fluid into the spinning membrane separator via the filtrate outlet port, controlling the pump system during a second stage to convey the priming fluid into the spinning membrane separator via the inlet port so as to convey air out of the spinning membrane separator via the retentate outlet port.

2. The fluid processing device of claim 1, wherein the controller is programmed to control the pump system to prevent flow out of the spinning membrane separator via the filtrate outlet port during the second stage.

3. The fluid processing device of claim 1, further comprising a weight scale, wherein the controller is programmed to control the pump system to stop conveying the priming fluid into the spinning membrane separator via the filtrate outlet port based at least in part upon a signal received by the controller from the weight scale.

4. The fluid processing device of claim 3, wherein the weight scale is configured to measure the weight of priming fluid conveyed out of the spinning membrane separator via the retentate outlet port during the first stage.

5. The fluid processing device of claim 1, wherein
the pump system includes a first pump associated with the inlet port and a second pump associated with the filtrate outlet port, and
the rate of flow through the retentate outlet port is equal to the difference between the operational rates of the first and second pumps.

6. The fluid processing device of claim 5, wherein
the controller is programmed to control the first pump to operate at a first operational rate during the first stage,
the controller is programmed to control the first pump to operate at a second operational rate during the second stage, and
the first and second operational rates are different.

7. The fluid processing device of claim 6, wherein the second operational rate is greater than the first operational rate.

8. The fluid processing device of claim 6, wherein
the controller is programmed to control the second pump to operate at a third operational rate during the first stage, and
the third operational rate is greater than the second operational rate.

9. The fluid processing device of claim 1, wherein the controller is programmed to control the spinning membrane separator drive unit to rotate the rotor within the housing during the first and second stages.

10. The fluid processing device of claim 1, wherein the controller is programmed to control the spinning membrane separator drive unit to rotate the rotor within the housing at the same rotational rate during the first and second stages.

11. A method of priming a spinning membrane separator including a housing, a rotor rotatably received within the housing, an inlet port, a filtrate outlet port in fluid communication with an interior of the rotor, and a retentate outlet port in fluid communication with an annulus defined between the housing and the rotor, the method comprising:
conveying a priming fluid into the spinning membrane separator via the filtrate outlet port during a first stage so as to convey air out of the spinning membrane separator via the inlet port and the retentate outlet port; and
ending the first stage; and
after ending the first stage, conveying the priming fluid into the spinning membrane via the inlet port during a second stage so as to convey air out of the spinning membrane separator via the retentate outlet port.

12. The method of claim 11, wherein flow out of the spinning membrane separator via the filtrate outlet port is prevented during the second stage.

13. The method of claim 11, wherein the first stage is ended based at least in part on a volume of priming fluid conveyed out of the spinning membrane separator via the retentate outlet port during the first stage.

14. The method of claim 11, wherein
the priming fluid is pumped into the spinning membrane separator via the filtrate outlet port and pumped out of the spinning membrane separator via the inlet port during the first stage, and
the rate of flow through the retentate outlet port during the first stage is equal to the difference between the rate at which the priming fluid is pumped into the spinning membrane separator via the filtrate outlet port and the rate at which the priming fluid is pumped out of the spinning membrane separator via the inlet port.

15. The method of claim 14, wherein the priming fluid is pumped out of the spinning membrane separator via the inlet port at a greater rate than the rate of flow through the retentate outlet port during the first stage.

16. The method of claim 14, wherein the priming fluid is pumped out of the spinning membrane separator via the inlet port during the first stage at a rate that is different from the rate at which the priming fluid is pumped into the spinning membrane separator via the inlet port during the second stage.

17. The method of claim 16, wherein the rate at which the priming fluid is pumped into the spinning membrane separator via the inlet port during the second stage is greater than the rate at which the priming fluid is pumped out of the spinning membrane separator via the inlet port during the first stage.

18. The method of claim 16, wherein the rate at which the priming fluid is pumped into the spinning membrane separator via the filtrate outlet port during the first stage is greater than the rate at which the priming fluid is pumped into the spinning membrane separator via the inlet port during the second stage.

19. The method of claim 11, further comprising rotating the rotor within the housing during the first and second stages.

20. The method of claim 19, wherein the rotor is rotated within the housing at the same rotational rate during the first and second stages.

21. The fluid processing device of claim 1, wherein
the filtrate outlet port is positioned at an upper end of the spinning membrane separator during the priming procedure, and
the controller is programmed to control the pump system during the first stage to convey the priming fluid into the spinning membrane separator via the filtrate outlet port in a downward direction.

22. The method of claim 11, further comprising orienting the spinning membrane separator so as to position the filtrate outlet port at an upper end of the spinning membrane separator before beginning the first stage, wherein said conveying the priming fluid into the spinning membrane separator via the filtrate outlet port during the first stage includes conveying the priming fluid into the spinning membrane separator via the filtrate outlet port in a downward direction.

* * * * *